(12) United States Patent
Baril et al.

(10) Patent No.: US 11,627,988 B2
(45) Date of Patent: Apr. 18, 2023

(54) SNAP-FIT CUTTING GUARD

(71) Applicant: Covidien LP, Mansfield, MA (US)

(72) Inventors: Jacob C. Baril, Norwalk, CT (US);
Scott J. Prior, Shelton, CT (US);
Saumya Banerjee, Hamden, CT (US);
Matthew A. Dinino, Newington, CT (US); Justin J. Thomas, New Haven, CT (US)

(73) Assignee: Covidien LP, Mansfield, MA (US)

( * ) Notice: Subject to any disclaimer, the term of this patent is extended or adjusted under 35 U.S.C. 154(b) by 177 days.

(21) Appl. No.: 16/928,660

(22) Filed: Jul. 14, 2020

(65) Prior Publication Data

US 2022/0015803 A1 Jan. 20, 2022

(51) Int. Cl.
*A61B 17/34* (2006.01)
*A61B 90/00* (2016.01)

(52) U.S. Cl.
CPC ...... *A61B 17/3494* (2013.01); *A61B 17/3423* (2013.01); *A61B 2090/036* (2016.02); *A61B 2217/005* (2013.01)

(58) Field of Classification Search
CPC .......... A61B 17/3423; A61B 2090/036; A61B 17/3494; A61B 2218/008; A61B 17/345; A61B 17/00234; A61B 2017/3425; A61B 2017/3427; A61B 2017/3429; A61B 17/3421; A61M 2039/0276; A61M 2039/0282; A61M 2039/0297; A61M 39/02; A61M 39/0247
USPC .......... 604/332, 334, 338; 600/208; 606/172
See application file for complete search history.

(56) References Cited

U.S. PATENT DOCUMENTS

| | | | |
|---|---|---|---|
| 5,578,000 A | 11/1996 | Greff et al. | |
| 5,941,873 A | 8/1999 | Korenfeld | |
| 6,033,362 A | 3/2000 | Cohn | |
| 6,544,210 B1 | 4/2003 | Trudel et al. | |
| 7,789,946 B2 | 9/2010 | Schultz et al. | |
| 7,901,353 B2 | 3/2011 | Vayser et al. | |
| 9,427,288 B1 | 8/2016 | Chenger et al. | |
| 10,076,358 B2 | 9/2018 | Zergiebel et al. | |
| 2005/0054993 A1 | 3/2005 | Falahee | |
| 2006/0247673 A1* | 11/2006 | Voegele | A61B 17/4241 606/191 |
| 2007/0151566 A1* | 7/2007 | Kahle | A61B 5/08 128/856 |
| 2012/0089093 A1 | 4/2012 | Trusty | |
| 2013/0184536 A1 | 7/2013 | Shibley et al. | |
| 2014/0330285 A1 | 11/2014 | Rosenblatt et al. | |
| 2016/0158468 A1 | 6/2016 | Tang et al. | |
| 2017/0049427 A1 | 2/2017 | Do et al. | |
| 2017/0325657 A1 | 11/2017 | Prior | |
| 2018/0008250 A1 | 1/2018 | Joseph | |

(Continued)

*Primary Examiner* — Melanie R Tyson
*Assistant Examiner* — Bridget E. Rabaglia
(74) *Attorney, Agent, or Firm* — Carter, DeLuca & Farrell LLP

(57) ABSTRACT

A tissue guard includes a body defining an open proximal end, an open distal end, and a lumen extending through the body between the open proximal end and the open distal end. A lip extends radially outwardly from the open proximal end of the body, the lip including a finger extending from an exterior peripheral surface thereof. The finger includes a flange at a distal end thereof adapted to operably engage an underside of a proximal ring of an access device to secure the tissue guard therein.

20 Claims, 7 Drawing Sheets

(56) References Cited

U.S. PATENT DOCUMENTS

2018/0049771 A1    2/2018  Rhemrev-Pieters
2019/0110786 A1*  4/2019  Ip ............................ A61B 17/02
2021/0361321 A1*  11/2021  Baril ....................... A61B 90/04

* cited by examiner

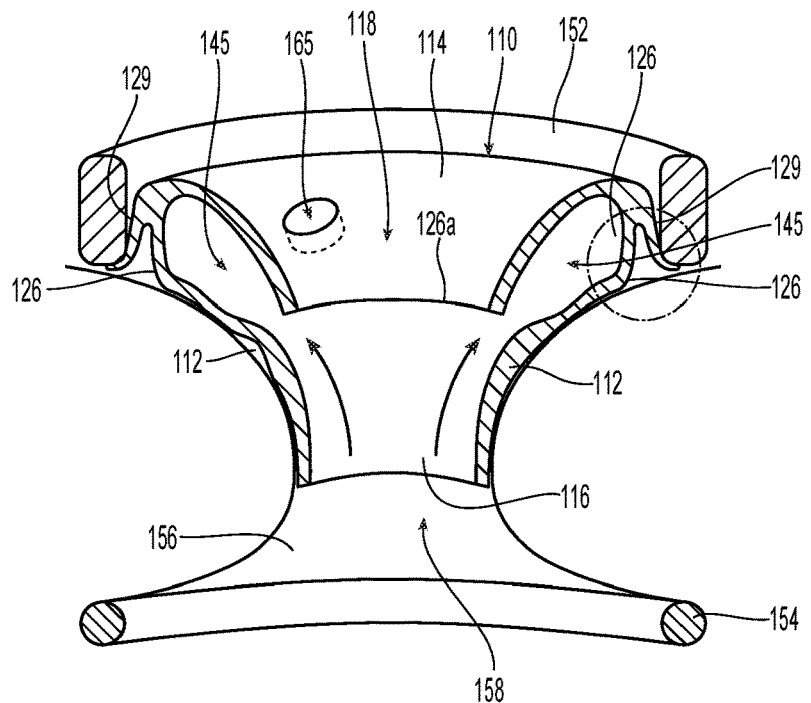
*Fig. 2A*
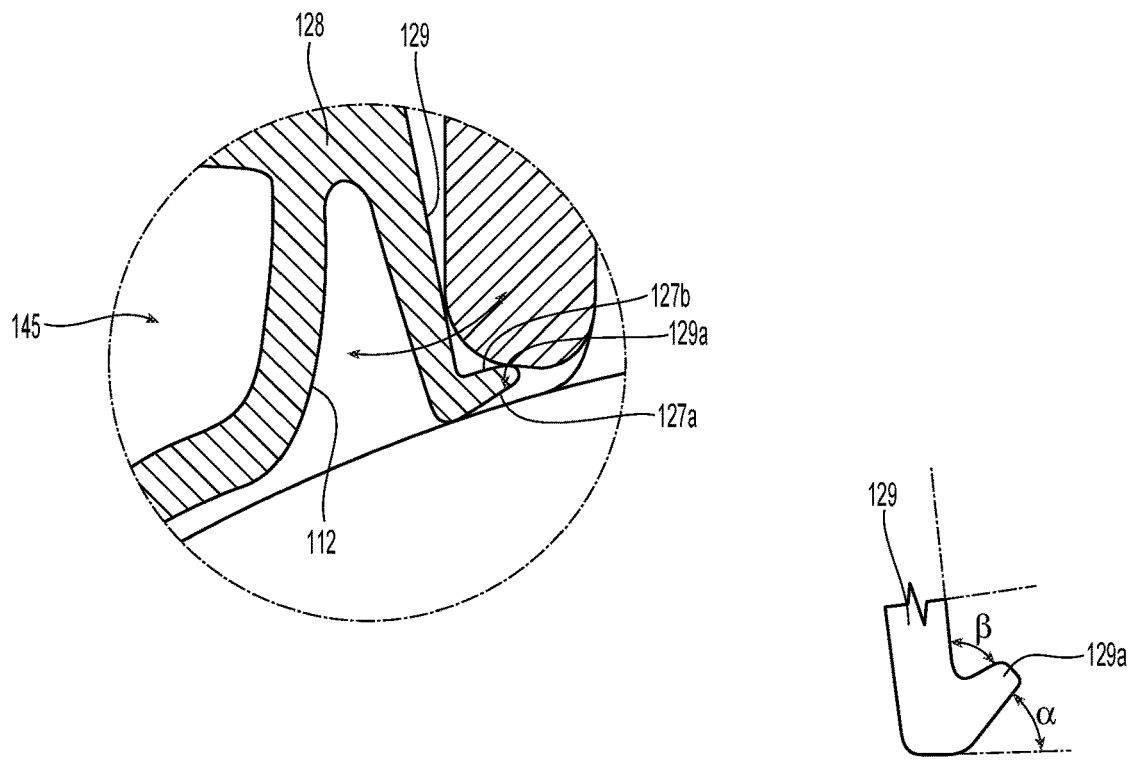
*Fig. 2B*
*Fig. 2C*

SNAP-FIT CUTTING GUARD

FIELD

The present disclosure relates to tissue specimen removal and, more particularly, to tissue guards and systems incorporating the same for use in tissue specimen removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard including a body defining an open proximal end, an open distal end, and a lumen extending through the body between the open proximal end and the open distal end. A lip extends radially outwardly from the open proximal end of the body, the lip including a finger extending from an exterior peripheral surface thereof. The finger includes a flange at a distal end thereof adapted to operably engage an underside of a proximal ring of an access device to secure the tissue guard therein.

In aspects according to the present disclosure, the finger is movable between a first configuration to facilitate insertion of the tissue guard within the access device and a second configuration wherein the flange operably engages the underside of the proximal ring. In other aspects according to the present disclosure, the finger is biased towards the second configuration.

In aspects according to the present disclosure, the flange includes an interior angle in the range of about 75 degrees to about 90 degrees to facilitate engagement of the flange with the underside of the proximal ring. In other aspects according to the present disclosure, the flange includes an exterior angle in the range of about 45 degrees to about 60 degrees to facilitate insertion of the tissue guard within the access device.

In aspects according to the present disclosure, the lip includes a distal end that extends inwardly towards the lumen to form an annular channel defined therein configured to direct surgical exhaust and surgical fluids from an operating cavity to a port defined in an outer peripheral surface of the lip.

In aspects according to the present disclosure, the tissue guard is made from a material resistant to cuts or tears from surgical instrumentation. In other aspects according to the present disclosure, the lip includes a port defined therein adapted to connect to a fluid management system.

Provided in accordance with other aspects of the present disclosure is a surgical system including an access device having a proximal end portion, a distal end portion, and a body extending between the proximal and distal end portions, the body defining a passageway extending therethrough. The proximal end portion defines a ring extending radially-inwardly into the passageway. A tissue guard is included that has a body defining an open proximal end, an open distal end, and a lumen extending through the body between the open proximal end and the open distal end. A lip extends radially outwardly from the open proximal end of the body, the lip including a finger extending from an exterior peripheral surface thereof. The finger includes a flange at a distal end thereof adapted to operably engage an underside of the proximal ring of the access device to secure the tissue guard therein.

In aspects according to the present disclosure, the flange of the finger of the tissue guard is configured to snap into engagement beneath the underside of the proximal ring of the access device. In other aspects according to the present disclosure, a fluid management system is included and the lip includes a port defined therein configured to operably engage the fluid management system.

Provided in accordance with another aspects of the present disclosure is a tissue guard including a body defining an open proximal end, an open distal end, and a lumen extending through the body between the open proximal end and the open distal end. A lip extends radially outwardly from the open proximal end of the body, the lip including one or more fingers that extend from an exterior peripheral surface thereof. The one or more fingers includes a flange at a distal end thereof that is adapted to mount atop a proximal ring of an access device such that the flange operably engages an underside of the proximal ring to secure the tissue guard therein.

In aspects according to the present disclosure, the flange extends inwardly relative to the proximal ring and operably engages the underside of the proximal ring when biased inwardly.

In aspects according to the present disclosure, the flange includes an interior angle in the range of about 75 degrees to about 90 degrees to facilitate engagement of the flange with the underside of the proximal ring. In other aspects according to the present disclosure, the flange includes an exterior angle in the range of about 45 degrees to about 60 degrees to facilitate insertion of the tissue guard within the access device.

In aspects according to the present disclosure, the tissue guard is made from a material resistant to cuts or tears from surgical instrumentation.

Provided in accordance with another aspects of the present disclosure is a tissue guard including a body including a first section and a second section each defining an open proximal end, an open distal end, and a lumen extending therethrough. The distal end of the first section includes a plurality of grooves defined therein and the proximal end of the second section includes a corresponding plurality of threads disposed thereon configured to operably engage the grooves to form the body, wherein relative rotation of the first section relative to the second section adjusts the height of the body when disposed within an access device.

In aspects according to the present disclosure, the body, when assembled, includes a hour-glass shape to facilitate engagement within the access device. In other aspects according to the present disclosure the distal end of the first section includes plurality of slots defined therein configured to allow the distal end of the first section to flare atop an outer peripheral surface of the second section during height adjustment of the body. In still other aspects according to the present disclosure, the proximal end of the tissue guard is configured to engage a proximal rim of the access device such that once the height of the body is established via rotation of the first section relative to the second section, the tissue guard can be secured to the access device.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

FIG. 2A is a front cross sectional view of the access device with the tissue guard inserted therein;

FIG. 2B is an enlarged view of the area of detail of FIG. 2A;

FIG. 2C is a greatly-enlarged view showing the engagement of a proximal flange of the tissue guard within a proximal rim the access device;

DETAILED DESCRIPTION

Figure 1A:
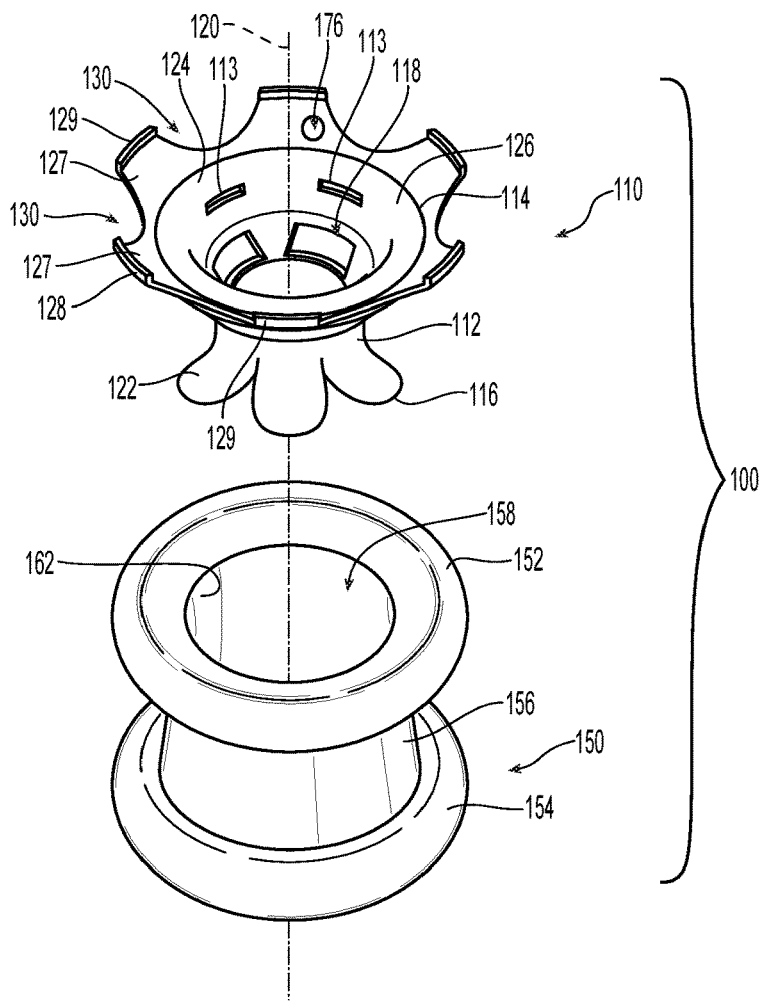
FIG. 1A is an exploded, top, perspective view of a system provided in accordance with the present disclosure including an access device and a tissue guard.
Figure 1B:
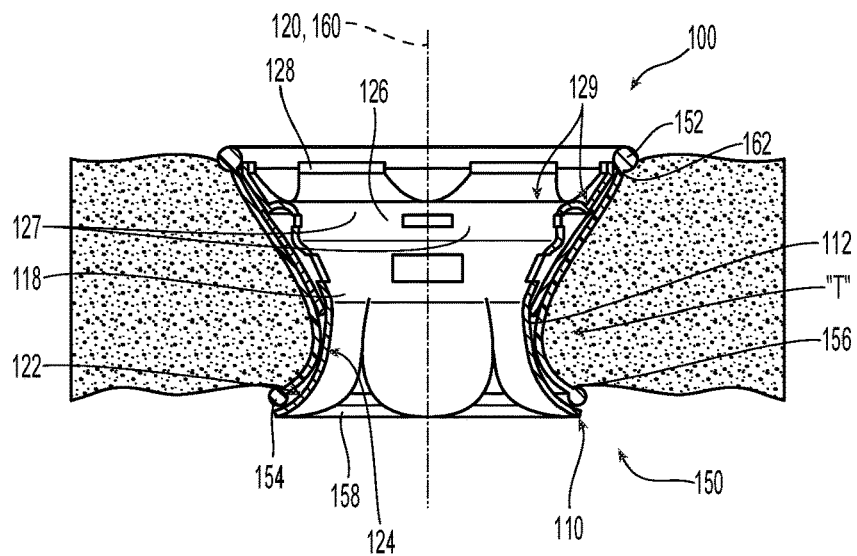
FIG. 1B is a cross-sectional view of the system of FIG. 1A disposed within an opening in tissue.

Turning to FIGS. 1A and 1B, a system 100 provided in accordance with the present disclosure includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration.

Access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 may further define an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Turing now to FIGS. 2A-2B, tissue guard 110 includes a lip 126 extending radially outwardly from open proximal end 114 of body 112 about the annular perimeter thereof. In this manner, lip 126 extends radially outwardly from lumen 118. Lip 126 may extend radially outwardly from body 112 at an oblique angle relative thereto. Lip 126 also includes an annular finger 129 extending from an outer peripheral surface thereof that is configured to anchor the tissue guard 110 within the access device 150. More particularly, annular finger 129 includes a flange 129a disposed at a distal end thereof that is configured to engage an underside of rim 152 of access device 150 to secure the tissue guard 110 therein. Finger 129 is configured to flex between an insertion position wherein the finger 129 is disposed in an abutting relationship with body 112 and a locking position wherein finger 129 flexes under a bias to engage flange 129a under rim 152 (FIG. 2B).

Flange 129a is angled to both facilitate insertion and to facilitate engagement. More particularly, an outer peripheral surface 127a of flange 129a is disposed at a first angle alpha ($\alpha$) in the range from about 75 degrees to about 90 degrees to encourage the finger 129 and, hence, the tissue guard 110, to slip into lumen 118 and an inner peripheral surface 127b is disposed at second angle beta ($\beta$) in the range from about 45 degrees to about 60 degrees to facilitate engagement of flange 129a with the underside of rim 152 (FIGS. 2B and 2C).

In embodiments, finger 129 may be configured to "snap" into engagement with the underside of rim 152 and, in such embodiments, may produce an audible and/or tactile response that confirms the engagement of tissue guard 110 within access device 150.

With tissue guard 110 engaged within access device 150 as detailed above, surgical instrumentation may be inserted through lumen 118 of tissue guard 110 into the internal surgical site to, for example, extract a tissue specimen therefrom. Tissue guard 110, as noted above, protects tissue "T" as well as access device 150 during the insertion, manipulation, use and withdrawal of any such surgical instrumentation.

Figure 3A:
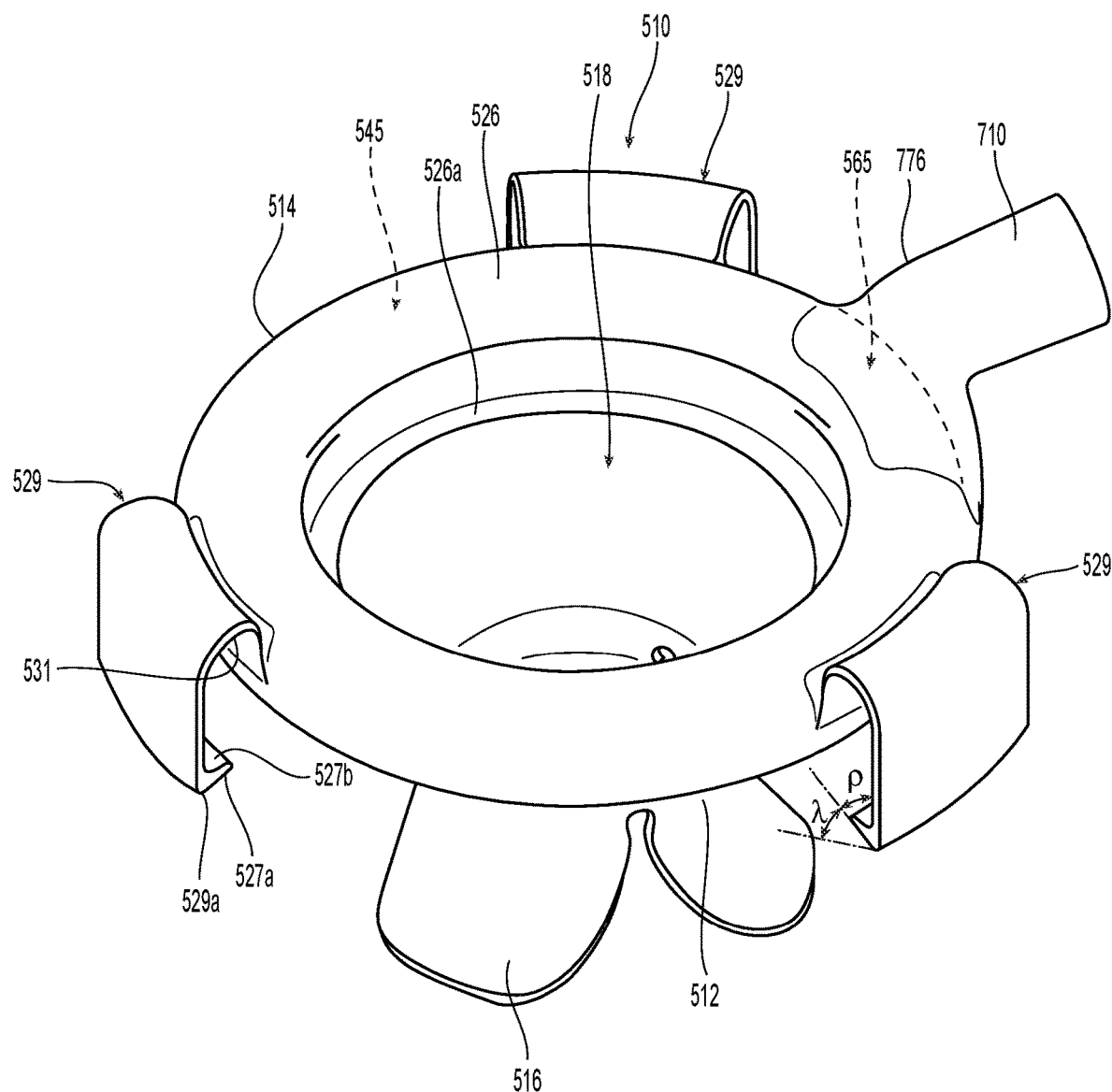
FIG. 3A is a top perspective view of another embodiment of a tissue guard for use with the access device.
Figure 3B:
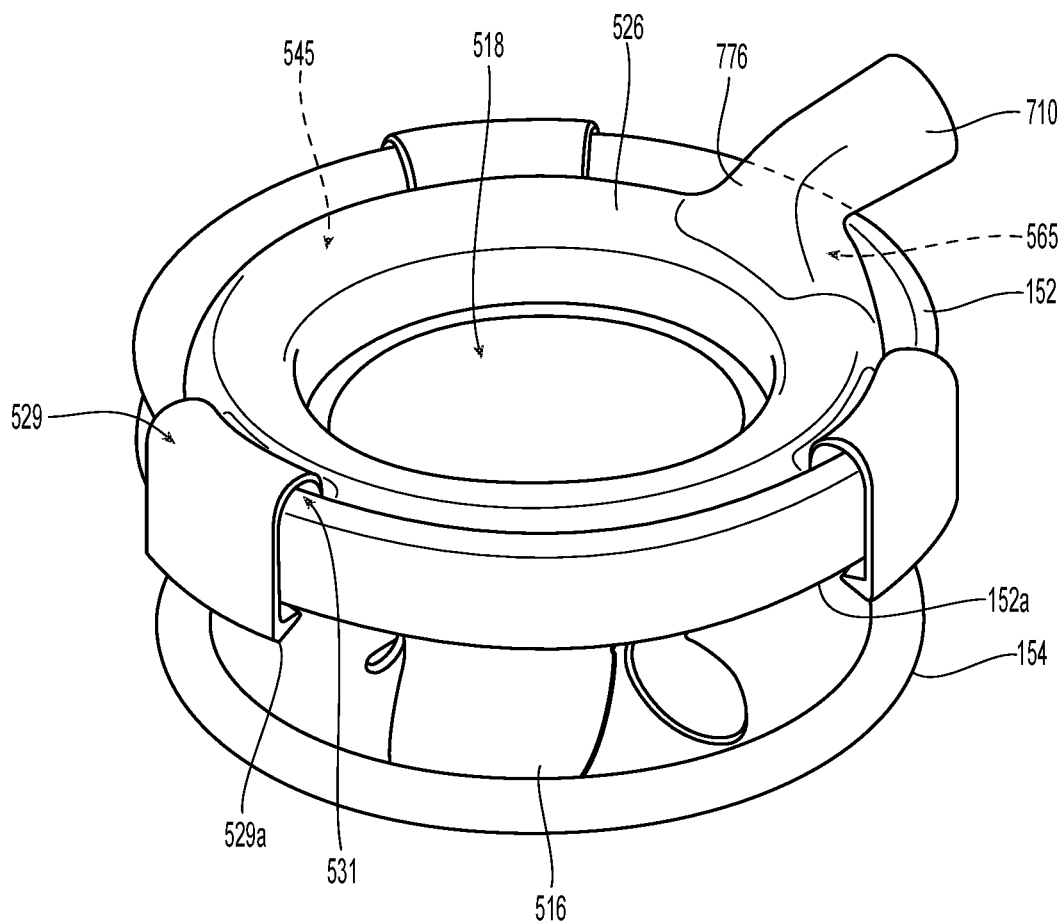
FIG. 3B is a top perspective view of the tissue guard of FIG. 3A engaged to a proximal rim of the access device.

Turning to FIGS. 3A-3B, another tissue guard 510 provided in accordance with the present disclosure is shown. With additional momentary reference to FIG. 2A, tissue guard 510 is similar to tissue guard 110 except as explicitly contradicted below and may be used in conjunction with access device 150 as part of a system similar to system 100. For purposes of brevity, only differences between tissue guard 510 and tissue guard 110 are detailed below, while similarities are summarily described or omitted.

Tissue guard 510 includes a body 512 defining an open proximal end 514, an open distal end 516, and a lumen 518 extending therebetween. A lip 526 extends radially outwardly from open proximal end 514 of body 512 and includes a plurality of fingers 529 extending from an outer peripheral surface thereof. The fingers 529 may be equidistantly-spaced about the lip 526 or may be spaced an any particular manner depending upon a particular purpose. In embodiments, a continuous finger (not shown) may be annularly spaced about the lip 526.

Each finger 529 includes an arcuate channel 531 defined along an inner peripheral surface thereof configured to at least partially encapsulate or mount atop rim 152 of the access device 150. More particularly, when the tissue guard 510 is first inserted into access device 150, channel 531 of each finger 529 aligns atop rim 152 of access device 150 and is poised for engagement atop rim 152 when the fingers 529 are secured. Each finger 529 also includes a flange 529a disposed at a distal end thereof that is configured to engage an underside of rim 152 to secure the tissue guard 510 in place. Finger 129 is configured to flex upon insertion of the tissue guard 510 into access device 150 by virtue of rim 152 forcing flange 529a and finger 529 outwardly as the tissue guard 510 is inserted. Upon full insertion of the tissue guard into access device, the channel 531 of finger 529 encapsulates the rim 152 while the flange 529a snaps into place under rim 152 thereby locking the tissue guard 510 atop access device 150. The finger 529 is biased in the locked position. The flange 529a extends inwardly relative to the proximal ring 152 and operably engages the underside of the proximal ring 152 when biased.

Flange 529a may be angled to both facilitate insertion and to facilitate engagement. More particularly, an outer peripheral surface 527a of flange 529a may be disposed at a first angle lamda ($\lambda$) in the range from about 45 degrees to about 60 degrees to encourage the finger 529 and, hence, the tissue guard 510, to slip into lumen 518 and an inner peripheral surface 527b is disposed at a second angle phi ($\varphi$) in the range from about 75 degrees to about 85 degrees to facilitate engagement of flange 529a with the underside of rim 152 (FIG. 3B). The shape of channel 531 may be dimensioned to conform to the shape of the outer peripheral surface of rim 152. Moreover, the height of the channel 531 may be dimensioned slightly larger than the thickness and depth of the rim 152 to facilitate engagement.

The distal end 516 of tissue guard 510 includes a plurality of scallop-like tabs 516a spaced-apart annularly thereabout. Scallop-like tabs 516a are configured engage an inner peripheral surface of body 112 of the access device 150 and are contoured or scalloped to generally mimic the shape thereof. The scallop-like tabs 516a are biased outwardly to maximize the opening at the distal end 516 of the tissue guard 510 and effectively secure the distal end 516 of the tissue guard 510 within access device 150 thereby facilitating surgical instrument access to the body cavity.

Figure 4:
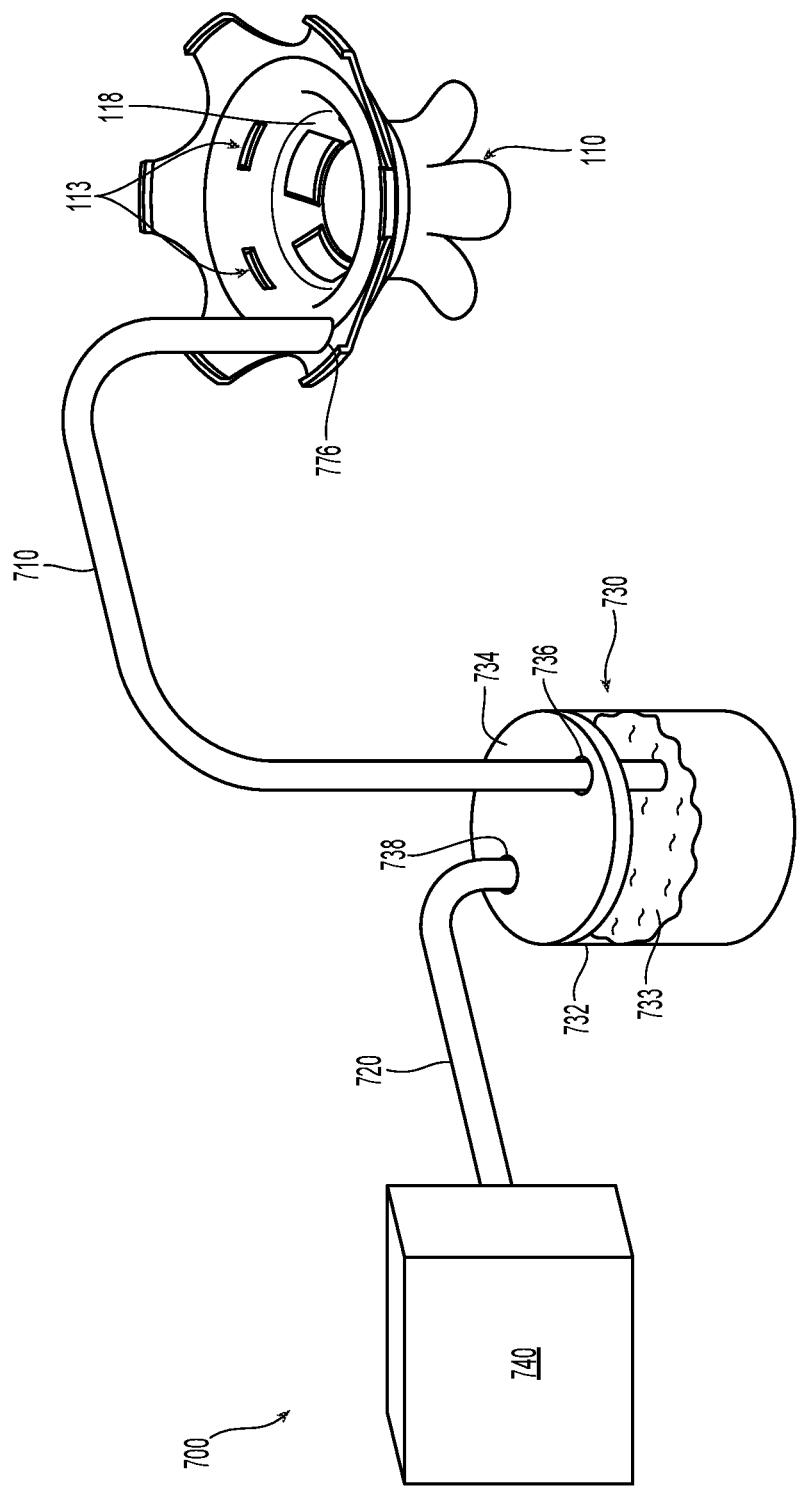
FIG. 4 is a system provided in accordance with the present disclosure including the tissue guard of FIGS. 2A-2C, tubing, a collection reservoir, and a smoke evacuation source.
Figure 5A:
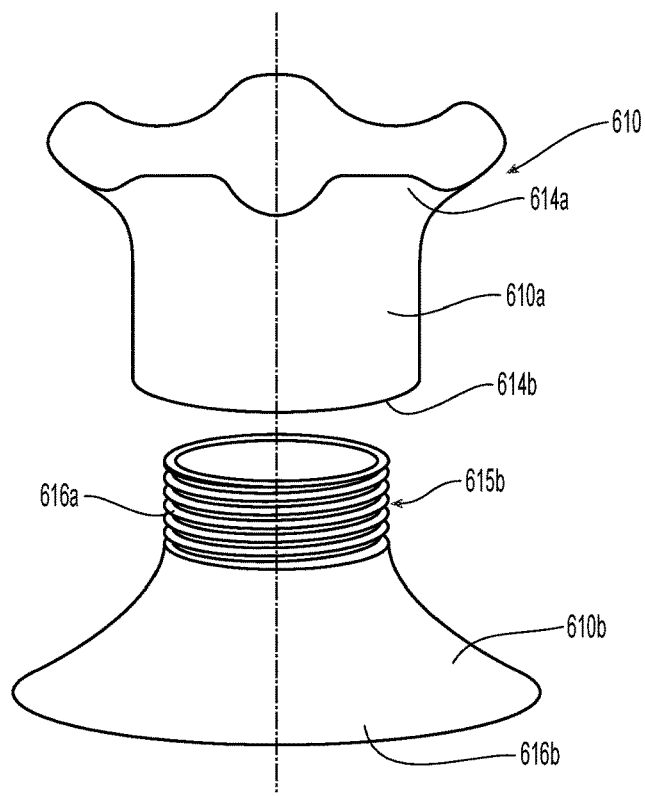
FIGS. 5A-5C are various views of a two piece embodiment of a tissue guard for use with the access device.
Figure 5B:
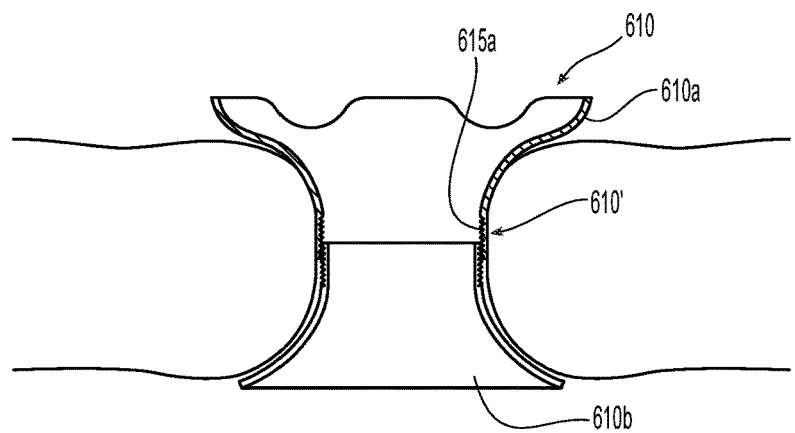
Figure 5C:
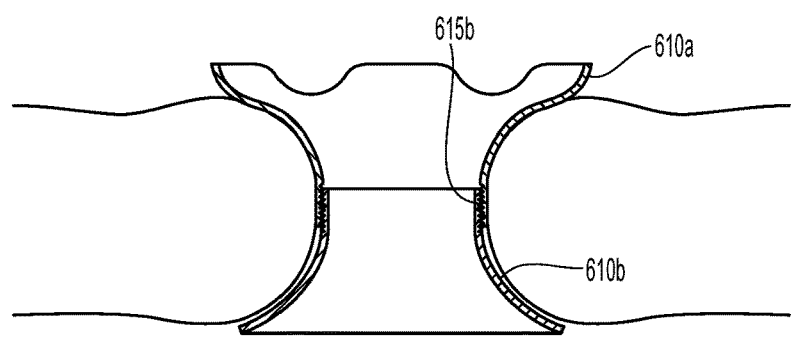

As mentioned above, and with reference to FIGS. 2A and 3A, lips 156, 526 define an annular channel therein configured to direct surgical exhaust therethrough to their respective ports 165, 565 defined in an outer peripheral surface of lips 126, 526. Lips 126, 526 include distal ends 126a, 526a that each extend inwardly therefrom toward lumens 118, 518 to form annular channels 145, 545 configured to direct surgical exhaust gas to ports 165, 565, respectively. One or more slits or passageways 113 (FIG. 4) may be defined within the inner peripheral surface of distal ends 126a, 526a that allow surgical gases passage into annular channels 145, 545, respectively. As explained in more detail below, each port 165, 565 is configured to connect to an exhaust connection 776 of a fluid management or smoke evacuation system 700 (FIG. 4). In other words, lips 126, 526 are each configured as generally hollow sleeves disposed proximate the inner peripheral surface of respective proximal ends 114, 514 of tissue guards 110, 510 and are configured to direct evacuation fluids and smoke to the exhaust connection 776 and to the fluid management or smoke evacuation system 700.

Turning to FIG. 4, smoke evacuation system 700 is provided in accordance with the present disclosure and is shown generally including tissue guard 110, tubing 710, 720, a collection reservoir 730, and a smoke evacuation (or vacuum) source 740. Tissue guard 510 works with smoke evacuation system in a similar fashion. The various tissue guards disclosed herein are all designed to work with system 700. Tissue guard 110 and tubing 710 are detailed above and are coupled to one another, e.g., via engagement of one end of tubing 710 about exhaust connection 776 of tissue guard 710. The other end of tubing 710 extends into collection reservoir 730 in sealing relation therewith.

Collection reservoir 730 includes a base 732 and a lid 734 sealed about base 732. Lid 734 defines first and second ports 736, 738 configured to receive ends of tubing 710, 720, respectively, in sealing relation therewith. These ends of tubing 710, 720 extend into the interior volume 733 of base 732 and are spaced-apart from one another as well as the bottom of base 732. Tubing 720 extends from collection reservoir 730 to smoke evacuation source 740 wherein the other end of tubing 720 is coupled to smoke evacuation source 740. In this manner, upon activation of smoke evacuation source 740, suction is established through lip 126 of tissue guard 110, tubing 710, collection reservoir 730, tubing 720, to smoke evacuation source 740. During use, this suction, in addition to evacuating smoke from tissue guard 110, may also suction liquids, tissue, and/or debris through tubing 710. However, as a result of the ends of tubing 710, 720 being spaced-apart from one another within collection reservoir 730 and spaced-apart from the bottom of base 732 of collection reservoir 730, the liquids, tissue, and/or debris are suctioned into collection reservoir 730 and deposited therein, while only the smoke and other gaseous fluids are further suctioned from collection reservoir 730 through tubing 720 to smoke evacuation source 740. As such, smoke evacuation source 740 is protected by inhibiting suctioning of liquids, tissue, and/or debris into smoke evacuation source 740.

FIGS. 5A-5E show another embodiment of a hour-glass shaped tissue guard 610 for use with the present disclosure. Although only the unique aspects of the tissue guard 610 are depicted in the figures, it is envisioned that tissue guard 610 may be used with any of the tissue guards described or referenced herein.

Tissue guard 610 includes first and second sections 610a and 610b, respectively that are configured to threadably engage one another to form tissue guard 610. Section 610a includes a proximal end 614a and a distal end 614b. Section 610b includes a proximal end 616a and a distal end 616b. Distal end 614b of section 610a includes a plurality of internal grooves 615a defined therein that is configured to threadably engage a corresponding plurality of threads 615b disposed on proximal end 616a of section 610b. When engaged the two sections form body 610' of tissue guard 610.

Once inserted in vivo, distal end 616b is configured to seat below passageway 158 of access device 150 with the proximal end 616a extending into passageway 158. In this manner, once the two sections 610a and 610b are threadably engaged, the hourglass design of tissue guard 610 insures a tight and secure fit within the access device 150. The hour glass design of tissue guard 610 also provides maximum incision area and provides greater visibility than conical shaped tissue guards.

The tissue guard 610a may be assembled in vivo simply by first inserting section 610b into access device 150 and then inserting section 610b into access device 150 and threadably coupling section 610a to section 610b. Moreover, the height or depth of tissue guard 610 may be selectively adjusted as needed simply by rotating section 610a relative to section 610b as described above. This will insure a secure fit within access device 150.

In embodiments, proximal end 614a may be configured to engage the access device 150 in a similar manner as described above. For example, distal end 616b may configured to seat below passageway 158 of access device 150 and once sections 610a and 610b are threadably engaged to form body 610', proximal end 614a of section 610a can be moved to engage rim 152 of access device 150 to secure the tissue guard 610 therein.

Similar to the tissue guards described above, tissue guard 610 may be made from any known flexible, cut resistant material to enable the tissue guard 610 to easily confirm to the internal passageway 158 of the access device 150.

Figure 6A:
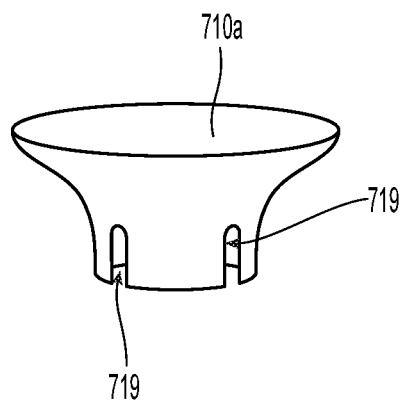
FIGS. 6A and 6B are various views of another embodiment of a first section of the two-piece tissue guard of FIGS. 5A-5C.
Figure 6B:
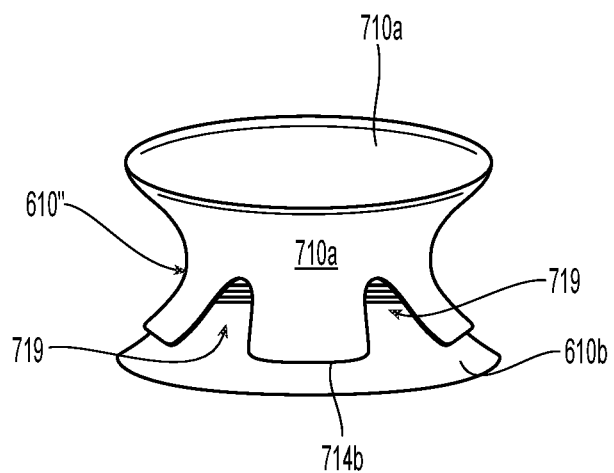

As best shown in FIGS. 6A and 6B, an expandable tissue guard section 710a may be utilized with section 610b. More particularly, section 710a may include a plurality of slots 719 defined in an outer peripheral surface of the distal end 714b. Slots 719 allow the distal end 714b of section 710a to flex outwardly as needed to permit further height adjustment of the tissue guard 610. More particularly, as section 710a is rotated relative to section 610b to reduce the height or depth of tissue guard 610, the slots 719 allow the distal end 714b of section 710a to flare outwardly atop the outer contour of section 610b to decrease the height or depth of the body 610" (made up of sections 710a and 610b) beyond the tissue guard 610 shown in FIGS. 5A-5C.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard, comprising:
a body defining an open proximal end portion, an open distal end portion, and a lumen extending through the body between the open proximal end portion and the open distal end portion; and
a lip including a proximal end extending radially outwardly from the open proximal end portion of the body and a distal end extending inwardly towards the lumen to form an annular channel having an annular opening into the lumen, the annular channel configured to direct surgical exhaust and surgical fluids from an operating cavity to a port defined in the lip;
a finger extending from an exterior peripheral surface of the lip; and
a flange disposed at a distal end portion of the finger, the flange tapering inwardly towards the lumen of the body from the finger to an inner edge of the flange to facilitate insertion and engagement of the tissue guard with an access device, the flange adapted to operably engage an underside of a proximal end portion of the access device to secure the tissue guard within the access device.

2. The tissue guard according to claim 1, wherein the finger is movable between a first configuration to facilitate insertion of the tissue guard within the access device and a second configuration wherein the flange operably engages the underside of the proximal end portion of the access device.

3. The tissue guard according to claim 2, wherein the finger is biased towards the second configuration.

4. The tissue guard according to claim 1, wherein the flange includes an interior angle in the range of 75 degrees to 90 degrees to facilitate engagement of the flange with the underside of the proximal end portion of the access device.

5. The tissue guard according to claim 1, wherein the flange includes an exterior angle in the range of 45 degrees to 60 degrees to facilitate insertion of the tissue guard within the access device.

6. The tissue guard according to claim 1, wherein the tissue guard is made from a material resistant to cuts or tears from surgical instrumentation.

7. The tissue guard according to claim 1, wherein the port is adapted to connect to a fluid management system.

8. The tissue guard according to claim 1, wherein the open distal end portion of the body is flared radially outwardly to facilitate engagement of the open distal end portion of the body with a distal end portion of the access device.

9. The tissue guard according to claim 1, wherein the flange is adapted to operably engage the underside of the proximal end portion of the access device from an exterior of the access device.

10. The tissue guard according to claim 1, wherein the finger has an inner surface defining an arcuate channel configured to engage the proximal end portion of the access device.

11. A surgical system, comprising:
an access device including a proximal end portion, a distal end portion, and a body portion extending between the proximal and distal end portions, the body portion defining a passageway extending therethrough, wherein the proximal end portion defines a ring extending radially-inwardly into the passageway; and
a tissue guard, including:
a body defining an open proximal end portion, an open distal end portion, and a lumen extending through the body between the open proximal end portion and the open distal end portion;
a lip including a proximal end extending radially outwardly from the open proximal end portion of the body and a distal end extending inwardly towards the lumen to form an annular channel having an annular opening into the lumen, the annular channel configured to direct surgical exhaust and surgical fluids from an operating cavity to a port defined in the lip;
a finger extending from an exterior peripheral surface of the lip; and
a flange disposed at a distal end portion of the finger, the flange tapering inwardly towards the lumen of the body from the finger to an inner edge of the flange to facilitate insertion and engagement of the tissue guard with the access device, the flange adapted to operably engage the ring of the access device to secure the tissue guard within the access device.

12. The system according to claim 11, wherein the flange of the finger of the tissue guard is configured to snap into engagement beneath an underside of the ring of the access device.

13. The system according to claim 11, further comprising a fluid management system, wherein the lip defines the port is configured to operably engage the fluid management system.

14. A tissue guard, comprising:
a body defining an open proximal end portion, an open distal end portion, and a lumen extending through the body between the open proximal end portion and the open distal end portion;
a lip extending radially outwardly from the open proximal end portion of the body and including a distal end extending inwardly towards the lumen to form an annular channel within the lip, the annular channel being in direct open communication with the lumen of the body and configured to direct surgical exhaust from an operating cavity to a port defined in the lip;
at least one finger extending from an exterior peripheral surface of the lip; and
a flange disposed at a distal end portion of the at least one finger, the flange diminishing in thickness along a length of the flange extending from the at least one finger to an inner edge of the flange, the at least one finger adapted to mount atop a proximal end portion of an access device such that the flange operably engages an underside of the proximal end portion of the access device to secure the tissue guard within the access device.

15. The tissue guard according to claim 14, wherein the flange extends inwardly relative to the proximal end portion of the access device and operably engages the underside of the proximal end portion of the access device when biased inwardly.

16. The tissue guard according to claim 14, wherein the flange includes an interior angle in the range of 45 degrees to 60 degrees to facilitate engagement of the flange with the underside of the proximal end portion of the access device.

17. The tissue guard according to claim 14, wherein the flange includes an exterior angle in the range of 75 degrees to 85 degrees to facilitate insertion of the tissue guard within the access device.

18. The tissue guard according to claim 14, wherein the tissue guard is made from a material resistant to cuts or tears from surgical instrumentation.

19. The tissue guard according to claim 14, wherein the at least one finger is adapted to mount atop a ring defined at the proximal end portion of the access device such that the flange operably engages an underside of the ring to secure the tissue guard within the access device, and wherein the lip is configured for positioning radially inwardly of the ring when the tissue guard is secured within the access device.

20. The tissue guard according to claim 14, wherein the at least one finger includes a plurality of fingers arranged annularly about the exterior peripheral surface of the lip.

* * * * *